(12) United States Patent
Doerr et al.

(10) Patent No.: US 12,728,276 B2
(45) Date of Patent: Sep. 8, 2026

(54) IMPLANTABLE SYSTEM AND METHOD FOR PROVIDING ANTI-TACHYCARDIA AND/OR SHOCK THERAPY

(71) Applicant: BIOTRONIK SE & Co. KG, Berlin (DE)

(72) Inventors: Thomas Doerr, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 280 days.

(21) Appl. No.: 18/683,963

(22) PCT Filed: Aug. 18, 2022

(86) PCT No.: PCT/EP2022/073113
§ 371 (c)(1),
(2) Date: Feb. 15, 2024

(87) PCT Pub. No.: WO2023/030913
PCT Pub. Date: Mar. 9, 2023

(65) Prior Publication Data

US 2024/0359023 A1 Oct. 31, 2024

(30) Foreign Application Priority Data

Sep. 6, 2021 (EP) .................................... 21194954

(51) Int. Cl.
*A61N 1/39* (2006.01)
*A61N 1/362* (2006.01)
*A61N 1/372* (2006.01)

(52) U.S. Cl.
CPC ....... *A61N 1/39622* (2017.08); *A61N 1/3621* (2013.01); *A61N 1/37217* (2013.01); *A61N 1/3925* (2013.01)

(58) Field of Classification Search
CPC .............. A61N 1/39622; A61N 1/3621; A61N 1/3925; A61N 1/37288; A61N 1/3756; A61N 1/3956
See application file for complete search history.

(56) References Cited

U.S. PATENT DOCUMENTS 5,836,971 A * 11/1998 Starkweather ....... A61N 1/3622 607/4
8,744,572 B1 * 6/2014 Greenhut ............. A61N 1/3621 607/4

(Continued)

FOREIGN PATENT DOCUMENTS

WO 2016126613 A1 8/2016

OTHER PUBLICATIONS

Extended European Search Report mailed Feb. 23, 2022, by the European Patent Office for Application No. EP21194954.0. (8 pages).

(Continued)

*Primary Examiner* — Paula J Stice
(74) *Attorney, Agent, or Firm* — Buchanan Ingersoll & Rooney PC

(57) ABSTRACT

An implantable system for providing anti-tachycardia and/or shock therapy, comprising an implantable pacing device, in particular an implantable leadless pacemaker, and an implantable cardioverter defibrillator, in particular a non-transvenous implantable cardioverter defibrillator, wherein the implantable pacing device is configured to detect a tachycardia and to provide anti-tachycardia pacing, wherein the implantable pacing device is further configured to signal an unavailability of anti-tachycardia pacing to the implantable cardioverter defibrillator, and wherein the implantable cardioverter defibrillator is configured, in response to the signal of the implantable pacing device, to adjust predetermined shock therapy parameters and/or to send a message to (Continued)

a remote monitoring system. A computer implemented method for providing anti-tachycardia and/or shock therapy, a computer program and a computer readable data carrier are also provided.

15 Claims, 4 Drawing Sheets

(56) References Cited

U.S. PATENT DOCUMENTS

| | | | | |
|---|---|---|---|---|
| 10,265,534 | B2 | 4/2019 | Greenhut et al. | |
| 2015/0360041 | A1* | 12/2015 | Stahmann | A61N 1/37205 607/4 |
| 2016/0008615 | A1 | 1/2016 | Stahmann et al. | |
| 2017/0312514 | A1* | 11/2017 | Hareland | A61N 1/3987 |
| 2018/0036547 | A1 | 2/2018 | Reddy | |
| 2018/0243578 | A1 | 8/2018 | Volosin | |
| 2019/0160285 | A1 | 5/2019 | Huelskamp et al. | |
| 2020/0254262 | A1* | 8/2020 | Demmer | A61N 1/3706 |

OTHER PUBLICATIONS

International Search Report (PCT/ISA/210) and Written Opinion (PCT/ISA/237) mailed Nov. 17, 2022, by the European Patent Office for International Application No. PCT/EP2022/073113. (17 pages).

* cited by examiner

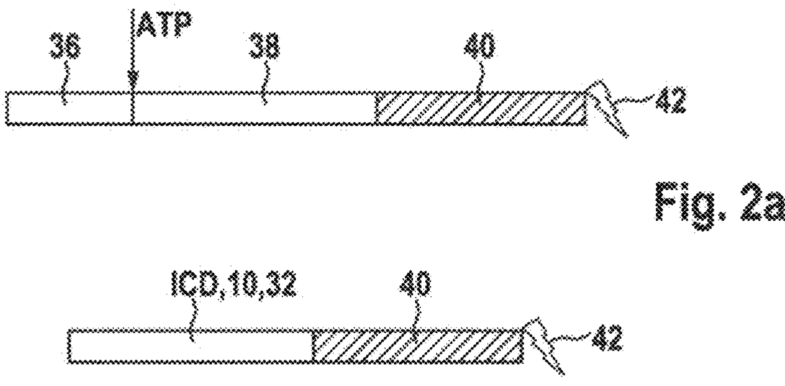
Fig. 2a
Fig. 2b
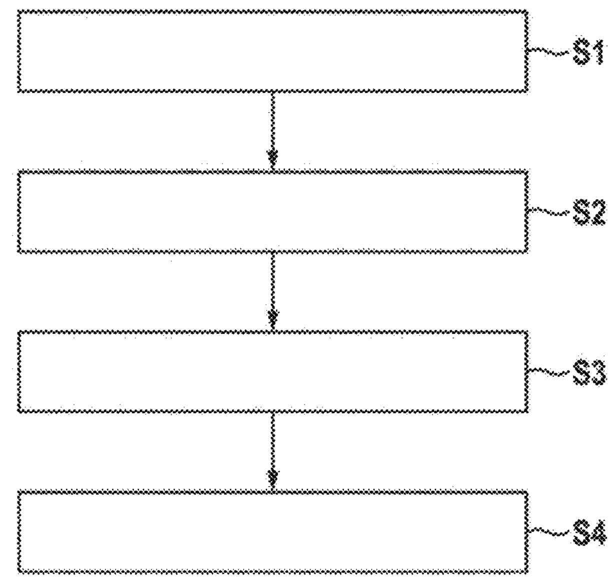
Fig. 3

IMPLANTABLE SYSTEM AND METHOD FOR PROVIDING ANTI-TACHYCARDIA AND/OR SHOCK THERAPY

CROSS-REFERENCE TO RELATED APPLICATIONS

This application is the United States National Phase under 35 U.S.C. § 371 of PCT International Patent Application No. PCT/EP2022/073113, filed on Aug. 18, 2022, which claims the benefit of European Patent Application No. 21194954.0, filed on Sep. 6, 2021, the disclosures of which are hereby incorporated by reference herein in their entireties.

TECHNICAL FIELD

The present invention relates to an implantable system for providing anti-tachycardia and/or shock therapy. Furthermore, the present invention relates to a computer implemented method for providing anti-tachycardia and/or shock therapy.

BACKGROUND

Such an implantable system also known as cardiac rhythm management system (CRMS) can be used for electric stimulation therapy of cardiac arrhythmia. Said cardiac rhythm management system comprises at least one first implantable stimulation device, for example, an implantable leadless pacemaker (iLP), and at least one second implantable stimulation device, for example, a subcutaneous implantable cardioverter defibrillator (S-ICD), wherein the at least one first implantable stimulation device comprises a first detection unit adapted to detect a patient's cardiac rhythm and a first processor adapted to analyze the detected patient's cardiac rhythm and to deliver signals for a first anti-tachycardia pacing therapy, wherein the at least one second implantable stimulation device comprises a second detection unit adapted to detect the patient's cardiac rhythm and a second processor adapted to analyze the detected patient's cardiac rhythm and to deliver signals for shock therapy.

Implantable stimulation devices such as implantable cardiac pacemakers or implantable leadless pacemakers are well known medical devices that allow stimulation of the heart of a patient. In general, those medical devices are battery operated and a stimulation component is directly implanted into the heart's ventricle or atrium. Implantable cardiac pacemakers have at least an elongated stimulation lead which reaches from the device housing into a heart chamber where it is anchored. Implantable leadless pacemakers are miniaturized pacing devices which are entirely implanted into the heart chamber.

Implantable stimulation devices with a defibrillation function are known in the art, as for instance implantable cardioverter-defibrillators (ICDs) or non-transvenous implantable cardioverter defibrillators, for example, subcutaneous implantable cardioverter-defibrillators (S-ICDs). Such devices typically comprise of a device housing and at least one elongated stimulation lead which extends from the housing. The housing of an ICD is typically implanted in a skin pocket below the clavicle, wherein the stimulation lead reaches into the ventricle of the heart where it is fixed. The housing and stimulation lead of an non-transvenous implantable cardioverter defibrillator are implanted under the skin (i.e., subcutaneously), in a way that a shock vector that runs through the cardiac ventricles is created between the stimulation electrode(s) of the lead and the non-transvenous implantable cardioverter defibrillator housing.

The medical device is chosen according to the patient's cardiac condition, i.e., the required cardiac therapy.

Implantable pacemakers or implantable leadless pacemakers are used for patients who suffer from a bradycardia, that is if a heart that beats too slow to fulfil the physiological needs of the patient. The implantable pacemaker or iLP applies electrical stimulation to the heart in order to generate a physiologically appropriate heartrate.

ICDs are used for patients who suffer from ventricular tachycardia and fibrillations. The ICD is able to apply anti-tachycardia pacing (ATP) therapy (i.e., pacing the heart with a faster stimulation rate than the tachycardia rate) to terminate a tachycardia, or a shock therapy (i.e., high energetic electric shock which is applied to the ventricles to terminate the tachycardia to bring back the heart to a physiological rhythm) if the tachycardia persists after ATP attempts.

Non-transvenous implantable cardioverter defibrillators are configured to deliver a shock therapy, but no pacing therapy or ATP therapy. That is due to the distance between stimulation lead and the cardiac chambers, so that a low energetic stimulation pulse could not be delivered effectively to a cardiac pacing site.

An iLP may deliver pacing therapy and ATP, but no shock therapy. Due to the highly restricted device size, it has a small battery capacity and lack of space for charging capacitors required for providing a shock therapy.

Moreover, implantable leads pose a risk to the patient and can therefore be a problem. The lead is an elongated insulated electrode wire which reaches from the device housing into the venous system of the heart where it is anchored in the ventricle. It undergoes different forces and movements with every beat of the heart, which can result in lead dislodgement, insulation failures and lead breach. That problem does not occur with non-transvenous implantable cardioverter defibrillators and implantable leadless pacemakers, because these devices have no intracardiac elongated lead. Especially for patients who have no adequate vascular access or are at high risk for infection, no elongated leads can be implanted inside the heart.

However, there are circumstances in which a patient suffers from various cardiac arrhythmias that require different cardiac therapies. In such cases, a CRMS may be implanted comprising at least two medical devices or units.

Furthermore, there exist cardiac arrhythmias for which different therapies are suitable and one treatment is more favorable, e.g., more comfortable, for the patient. Further, some therapies may cause another arrhythmia, so that an additional therapy is required in order to stop this arrhythmia. In practice, ventricular tachycardia, for example, may be treated using ATP therapy or shock therapy, wherein shock therapy is often uncomfortable for patients as the shocks are emitted unexpectedly and may be painful. In addition, shock therapies cause a considerable decrease in the longevity of the battery. Nevertheless, shock therapy is inevitable if a ventricular tachycardia leads to ventricular fibrillation as ATP therapy is not suitable to treat fibrillations.

For instance, a patient who has a contraindication for intracardiac elongated leads and who suffers from ventricular tachycardia requires pacing therapy, ATP and shock therapy. In such case, a CRMS may be implanted comprising at least a first implantable stimulation device and a second implantable stimulation device, wherein the first implantable stimulation device may be an implantable leadless pacemaker, and the second device a non-transvenous implantable cardioverter defibrillator.

According to another example, if a patient who has a contraindication for intracardiac elongated leads and who requires pacing therapy and/or ATP, in the ventricle (or at the HIS bundle) and in the atrium, a CRMS may be implanted comprising at least a first implantable stimulation device and a second implantable stimulation device, wherein the first implantable stimulation device may be a first implantable leadless pacemaker, and the second device a second implantable leadless pacemaker.

Cardiac rhythm management systems comprising multiple treatment therapies are, for example, provided by a combination of S-ICD and iLP as disclosed in the prior art documents U.S. Publication No. 2019/0160285 A1 and U.S. Pat. No. 10,265,534 B2. The coordination of such systems is obligatory in order to provide proper treatment as the therapies may be ineffective if they are applied simultaneously.

Furthermore, U.S. Publication No. 2016/0008615 A1 relates to a medical device system for delivering electrical stimulation therapy to a heart of a patient, the system comprising a leadless cardiac pacemaker LCP implanted within a heart of a patient and configured to determine occurrences of cardiac arrhythmias, a medical device configured to determine occurrences of cardiac arrhythmias and to deliver defibrillation shock therapy to the patient, wherein the LCP and the medical device are spaced from one another and communicatively coupled, and wherein after the LCP determines an occurrence of a cardiac arrhythmia, the LCP is configured to modify the defibrillation shock therapy of the medical device.

In addition, U.S. Publication No. 2018/0243578 A1 discloses an ambulatory medical device comprising at least one therapy electrode configured to couple externally to a skin of a patient and to provide one or more transthoracic therapeutic stimulation pulses to a heart of the patient, at least one sensing electrode configured to couple externally to the skin of the patient and to acquire electrocardiogram (ECG) signals from the patient, and at least one processor coupled to the at least one therapy electrode and the at least one sensing electrode and configured to process the ECG signals from the patient to detect a tachycardia condition in the heart of the patient, determine, in response to detecting the tachycardia condition, whether an implanted pacemaker restores the heart of the patient to a normal condition within a predetermined period, and provide the one or more transthoracic therapeutic stimulation pulses to the heart of the patient in response to determining that the implanted pacemaker failed to restore the heart of the patient to the normal condition within the predetermined period.

The above-mentioned cardiac rhythm management systems have in common that in order to coordinate ATP therapy by the iLP and defibrillation therapy by the ICD, a shock therapy delay by the ICD is required to ensure that ATP delivery by the iLP occurs first in lower tachycardia zones and therapy success can be assessed.

If, however, ATP therapy success fails to occur, defibrillation therapy is initiated by the ICD with the aforementioned delay. If, over time, the battery of the iLP becomes depleted and it can no longer deliver ATP or if a fault condition occurs in the iLP, the ICD would unnecessarily delay the required therapy in the event of tachycardia.

The present disclosure is directed toward overcoming one or more of the above-mentioned problems, though not necessarily limited to embodiments that do.

SUMMARY

It is therefore an object of the present invention to provide an improved implantable system for providing anti-tachycardia and/or shock therapy capable of avoiding a delay in therapy for defibrillation therapy of an ICD implanted in combination with an iLP with ATP whenever the iLP can no longer deliver ATP.

At least the object is solved by an implantable system for providing anti-tachycardia and/or shock therapy having the features of claim 1.

Furthermore, at least the object is solved by a computer implemented method for providing anti-tachycardia and/or shock therapy having the features of claim 13.

Moreover, at least the object is solved by a computer program having the features of claim 14 and a computer-readable data carrier having the features of claim 15.

Further developments and advantageous embodiments are defined in the dependent claims.

The present invention provides an implantable system for providing anti-tachycardia and/or shock therapy, comprising an implantable pacing device, in particular an implantable leadless pacemaker, and an implantable cardioverter defibrillator, in particular a non-transvenous implantable cardioverter defibrillator, wherein the implantable pacing device is configured to detect a tachycardia and to provide anti-tachycardia pacing, wherein the implantable pacing device is further configured to signal an unavailability of anti-tachycardia pacing to the implantable cardioverter defibrillator, and wherein the implantable cardioverter defibrillator is configured, in response to the signal of the implantable pacing device, to adjust predetermined shock therapy parameters and/or to send a message to a remote monitoring system.

Furthermore, the present invention provides a computer implemented method for providing anti-tachycardia and/or shock therapy.

The method comprises providing an implantable system for providing anti-tachycardia and/or shock therapy, comprising an implantable pacing device, in particular an implantable leadless pacemaker, and an implantable cardioverter defibrillator, in particular a non-transvenous implantable cardioverter defibrillator.

Furthermore, the method comprises detecting a tachycardia and providing anti-tachycardia pacing, by means of the implantable pacing device.

In addition, the method comprises signaling an unavailability of anti-tachycardia pacing to the implantable cardioverter defibrillator by means of the implantable pacing device and adjusting predetermined shock therapy parameters and/or to sending a message to a remote monitoring system by the implantable cardioverter defibrillator in response to the signal of the implantable pacing device.

Furthermore, the present invention provides a computer program with program code to perform the method of the present invention when the computer program is executed on a computer.

Moreover, the present invention provides a computer-readable data carrier containing program code of a computer program for performing the method of the present invention when the computer program is executed on a computer.

An idea of the present invention is to enable optimal therapy control in a distributed anti-tachycardia therapy system even in the event that a system component for ATP delivery can no longer deliver therapy.

According to the present invention, the pacemaker advantageously informs the implanted defibrillator that the pacemaker itself is no longer able to deliver an anti-tachycardic pacing, for example, due to battery exhaustion. The pacemaker thus communicates with the implanted defibrillator with the aim of the defibrillator adapting its therapy scheme.

According to an aspect of the present invention, the implantable pacing device is configured to stimulate at least one ventricle of a human or animal heart, wherein the implantable pacing device comprises a configurable tachyarrhythmia detection unit configured to detect a tachycardia and further comprises an anti-tachycardia pacing timing unit configured to deliver an anti-tachycardia pacing sequence in response to tachycardia detection.

An ATP sequence usually comprises 5-8 pacing pulses. These are delivered slightly faster than the actual detected tachycardia. The cycle length of the tachycardia is measured in the detection unit and then the timing of these 5-8 pulses is calculated in the timing unit, which have, for example, 80% of the cycle length of the tachycardia and thus effectively overstimulate said tachycardia.

According to a further aspect of the present invention, the implantable pacing device comprises a fault detection device configured to detect the unavailability of anti-tachycardia pacing, in particular due to a battery exhaustion and/or fault conditions of the implantable pacing device. Thus, the cause of the unavailability of anti-tachycardia pacing can advantageously be detected.

According to a further aspect of the present invention, the implantable pacing device comprises a first control unit configured to block anti-tachycardia pacing delivery after detection of battery exhaustion and/or fault conditions and is configured to signal the unavailability of anti-tachycardia pacing to the implantable cardioverter defibrillator. Therefore, if battery capacity and/or a fault condition make anti-tachycardia pacing unavailable, the provision of anti-tachycardia pacing delivery can effectively be blocked.

According to a further aspect of the present invention, the implantable pacing device is configured to detect a first stage of battery depletion, in which anti-tachycardia pacing is unavailable but anti-bradycardic pacing is available, and wherein the implantable pacing device is configured to detect a second stage of battery depletion, in which both anti-tachycardia pacing and anti-bradycardic pacing are unavailable. Thus, a corresponding therapy can be provided in accordance with a detected stage of battery depletion.

According to a further aspect of the present invention, the implantable pacing device is configured to signal the implantable cardioverter defibrillator by means of intra-body-communication, in particular by means of electrical pulses, communication and/or radio signals. Therefore, advantageously no cable-based connection needs to be present between the implantable pacing device and the implantable cardioverter defibrillator.

According to a further aspect of the present invention, the implantable pacing device is configured to signal the unavailability of anti-tachycardia pacing to the implantable cardioverter defibrillator by an absence of expected anti-tachycardia pacing, in particular if anti-tachycardia pacing is not provided for a predetermined time period in case of a detected tachycardia. This advantageously results in the provision of shock therapy without unnecessary delay should it be necessary.

According to a further aspect of the present invention, the implantable cardioverter defibrillator comprises at least one receiving unit configured to receive at least one information unit, in particular indicating the unavailability of anti-tachycardia pacing and/or anti-bradycardic pacing, from the implantable pacing device. Thus, advantageously the cause of the fault condition can be transmitted to the implantable cardioverter defibrillator.

According to a further aspect of the present invention, the implantable cardioverter defibrillator comprises a second control unit configured to adjust a therapeutic and/or diagnostic behavior of the implantable cardioverter defibrillator upon receiving the at least one information unit from the implantable pacing device and/or to forward the received at least one information unit to the remote monitoring system. The implantable cardioverter defibrillator can thus advantageously be adjusted according to the specific fault condition.

According to a further aspect of the present invention, the implantable cardioverter defibrillator is configured to detect the at least one information unit if one or more expected anti-tachycardia pacing attempts are not sensed by the implantable cardioverter defibrillator. This is a further criterion for enabling that the at least one information unit is received by the implantable cardioverter defibrillator.

According to a further aspect of the present invention, the implantable cardioverter defibrillator is configured to shorten or suppress a defibrillation delay when it is detected that anti-tachycardia pacing delivery is unavailable. Therefore, shock therapy can be administered faster without unnecessary delay.

According to a further aspect of the present invention, the implantable cardioverter defibrillator is configured to adjust at least one zone boundary for tachycardia detection when it is detected that anti-tachycardia pacing delivery is unavailable. This data can advantageously be taken into account in order to more accurately determine suitable detection zones.

The herein described features of the implantable system for providing anti-tachycardia and/or shock therapy are also disclosed for the computer implemented method for providing anti-tachycardia and/or shock therapy and vice versa.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

For a more complete understanding of the present invention and advantages thereof, reference is now made to the following description taken in conjunction with the accompanying drawings. The present invention is explained in more detail below using exemplary embodiments, which are specified in the schematic figures of the drawings, in which:

FIG. 2*a* shows a schematic view of a therapy sequence of an implantable system for providing anti-tachycardia and/or shock therapy which does not form part of the present invention;

FIG. 2*b* shows a schematic view of a therapy sequence of the implantable system for providing anti-tachycardia and/or shock therapy according to the preferred embodiment of the present invention;

FIG. 3 shows a flowchart of a computer implemented method for providing anti-tachycardia and/or shock therapy according to the preferred embodiment of the present invention.

DETAILED DESCRIPTION

Figure 1:
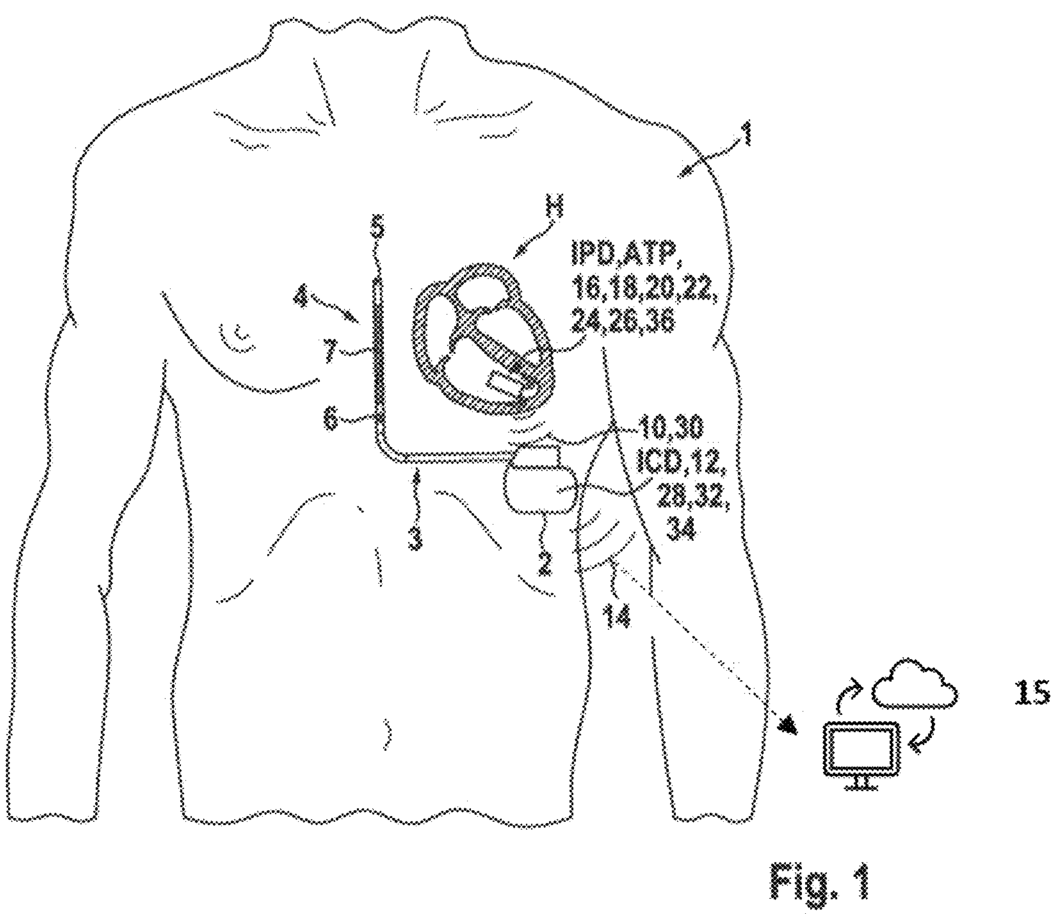
FIG. 1 shows a schematic view of an implantable system for providing anti-tachycardia and/or shock therapy according to a preferred embodiment of the present invention.

The implantable system 1 shown in FIG. 1 for providing anti-tachycardia and/or shock therapy comprises an implantable pacing device IPD, in particular an implantable leadless pacemaker, and an implantable cardioverter defibrillator ICD, in particular a non-transvenous implantable cardioverter defibrillator.

Figure 4:
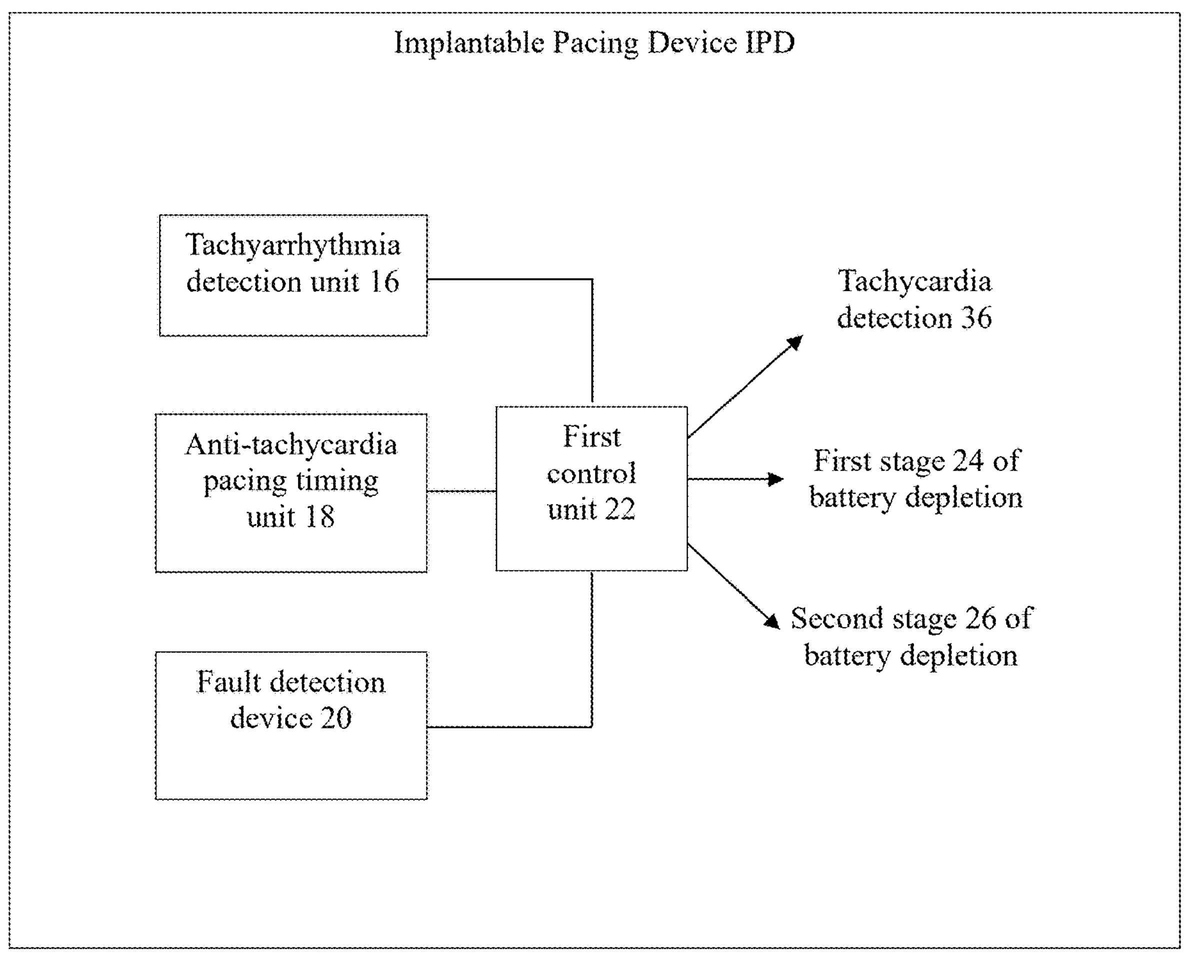
FIG. 4 shows an exemplary architecture block diagram of an implantable pacing device.

The implantable pacing device IPD comprises an active housing 2, an electrode lead 3 implanted subcutaneously along the sternum 4 and having two sensing poles 5, 6 and a shock 25 coil 7. FIG. 4 shows an architecture block diagram of the implantable pacing device IPD, illustrating the interrelation of its components: the tachyarrhythmia detection unit 16, the anti-tachycardia pacing timing unit 18, the fault detection device 20, and the first control unit 22, along with operation functions of the first stage 24 of battery depletion, the second stage 26 of battery depletion, and the tachycardia detection 36.

Figure 5:
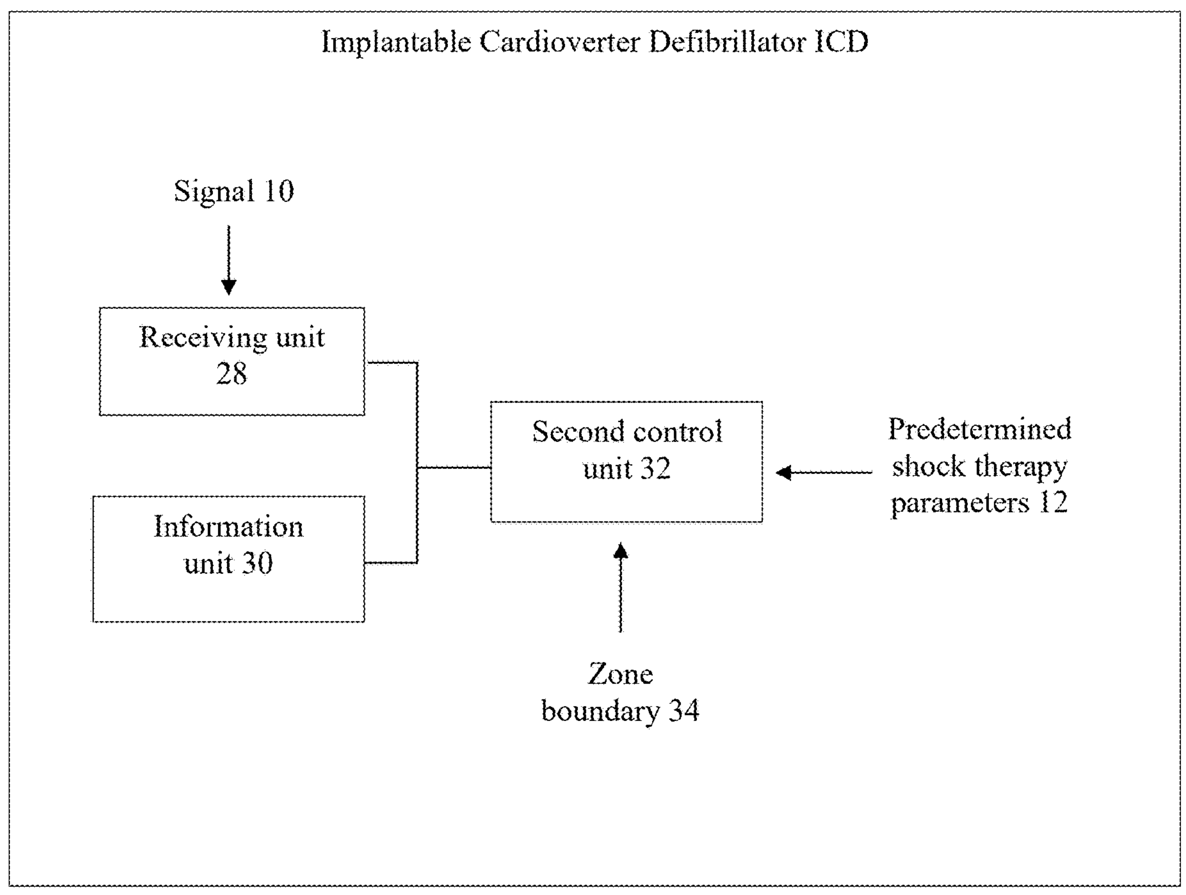
FIG. 5 shows an exemplary architecture block diagram of an implantable cardioverter defibrillator.

The implantable pacing device IPD is configured to detect a tachycardia and to provide anti-tachycardia pacing ATP, wherein the implantable pacing device IPD is further configured to signal 10 an unavailability of anti-tachycardia pacing ATP to the implantable cardioverter defibrillator ICD. FIG. 5 shows an architecture block diagram of the implantable cardioverter defibrillator ICD, illustrating the interrelation of its components: the information unit 30, the receiving unit 28, and the second control unit 32, along with operational functions of receicing the signal 10, the predetermined shock therapy parameters 12, and the zone boundary 34. Furthermore, the implantable cardioverter defibrillator ICD is configured, in response to the signal 10 of the implantable pacing device IPD, to adjust predetermined shock therapy parameters 12 and/or to send a message 14 to a remote monitoring system 15.

The implantable pacing device IPD is configured to stimulate at least one ventricle of a human or animal heart H. Moreover, the implantable pacing device IPD comprises a configurable tachyarrhythmia detection unit 16 configured to detect a tachycardia and further comprises an anti-tachycardia pacing timing unit 18 configured to deliver an anti-tachycardia pacing ATP sequence in response to tachycardia detection.

In addition, the implantable pacing device IPD comprises a fault detection device 20 configured to detect the unavailability of anti-tachycardia pacing ATP, in particular due to a battery exhaustion and/or fault conditions of the implantable pacing device IPD.

The implantable pacing device IPD comprises a first control unit 22 configured to block anti-tachycardia pacing ATP delivery after detection of battery exhaustion and/or fault conditions and is configured to signal 10 the unavailability of anti-tachycardia pacing ATP to the implantable cardioverter defibrillator ICD.

Moreover, the implantable pacing device IPD is configured to detect a first stage 24 of battery depletion, in which anti-tachycardia pacing ATP is unavailable but anti-bradycardic pacing is available. Furthermore, the implantable pacing device IPD is configured to detect a second stage 26 of battery depletion, in which both anti-tachycardia pacing ATP and anti-bradycardic pacing are unavailable.

In addition, the implantable pacing device IPD is configured to signal 10 the implantable cardioverter defibrillator ICD by means of intra-body-communication, in particular by means of electrical pulses, communication and/or radio signals.

Furthermore, the implantable pacing device IPD is configured to signal 10 the unavailability of anti-tachycardia pacing ATP to the implantable cardioverter defibrillator ICD by an absence of expected anti-tachycardia pacing ATP, in particular if anti-tachycardia pacing ATP is not provided for a predetermined time period in case of a detected tachycardia.

The implantable cardioverter defibrillator ICD comprises at least one receiving unit 28 configured to receive at least one information unit 30, in particular indicating the unavailability of anti-tachycardia pacing ATP and/or anti-bradycardic pacing, from the implantable pacing device IPD.

The implantable cardioverter defibrillator ICD comprises a second control unit 32 configured to adjust a therapeutic and/or diagnostic behavior of the implantable cardioverter defibrillator ICD upon receiving the at least one information unit 30 from the implantable pacing device IPD and/or to forward the received at least one information unit 30 to the remote monitoring system 15.

The implantable cardioverter defibrillator ICD is configured to detect the at least one information unit 30 if one or more expected anti-tachycardia pacing ATP attempts are not sensed by the implantable cardioverter defibrillator ICD. A predetermined time period, during which no signal is received by the implantable cardioverter defibrillator ICD from the implantable pacing device IPD can thus serve as information unit 30 for informing the implantable cardioverter defibrillator ICD that anti-tachycardia pacing ATP delivery is unavailable.

Furthermore, the implantable cardioverter defibrillator ICD is configured to shorten or suppress a defibrillation delay when it is detected that anti-tachycardia pacing ATP delivery is unavailable. The implantable cardioverter defibrillator ICD is further configured to adjust at least one zone boundary 34 for tachycardia detection when it is detected that anti-tachycardia pacing ATP delivery is unavailable.

A first therapy zone could be between 160-200 beats per minute. In this first zone only the anti-tachycardic stimulation is delivered. From 200 beats per minute on up the defibrillator also delivers a shock. If anti-tachycardia pacing is no longer available, the defibrillator would then deliver the shock already from, e.g., 160 beats per minute, i.e., adjust the zone limit accordingly.

FIG. 2*a* shows a schematic view of a therapy sequence of an implantable system for providing anti-tachycardia and/or shock therapy which does not form part of the present invention.

First, tachycardia detection 36 is performed—in parallel in the implantable pacing device and the implantable cardioverter defibrillator.

Following tachycardia detection 36, the implantable pacing device delivers anti-tachycardia pacing therapy, with the implantable cardioverter defibrillator initially withholding the initiation of shock therapy through a programmed therapy delay.

In the sequence outlined here, the anti-tachycardia pacing therapy is not effective and the ventricular tachycardia 38 continues to hold, so after the therapy delay expires, if the tachycardia continues, the implantable cardioverter defibrillator initiates a charging process for the shock capacitors 40 and delivers the shock therapy 42 after its completion.

FIG. 2*b* shows a schematic view of a therapy sequence of the implantable system 1 for providing anti-tachycardia and/or shock therapy according to the preferred embodiment of the present invention.

The implantable cardioverter defibrillator ICD receives a signal 10 from the implantable pacing device IPD that it cannot deliver anti-tachycardia pacing therapy henceforth.

The second control unit 32 of the implantable cardioverter defibrillator ICD then adjusts the therapy control of the implantable cardioverter defibrillator ICD in such a way that the therapy delay is now switched off and the implantable cardioverter defibrillator ICD starts the charging process of the shock capacitors 40 immediately after detection of the tachycardia and can thus deliver shock therapy 42 significantly earlier.

FIG. 3 shows a flowchart of a computer implemented method for providing anti-tachycardia and/or shock therapy according to the preferred embodiment of the present invention.

The method comprises providing S1 an implantable system 1 for providing anti-tachycardia and/or shock therapy, comprising an implantable pacing device IPD, in particular an implantable leadless pacemaker, and an implantable cardioverter defibrillator ICD, in particular a non-transvenous implantable cardioverter defibrillator;

Furthermore, the method comprises detecting S2 a tachycardia and providing anti-tachycardia pacing ATP, by means of the implantable pacing device IPD.

In addition, the method comprises signaling S3 an unavailability of anti-tachycardia pacing ATP to the implantable cardioverter defibrillator ICD by means of the implantable pacing device IPD, and adjusting S4 predetermined shock therapy parameters 12 and/or sending a message 14 to a remote monitoring system 15 by the implantable cardioverter defibrillator ICD in response to the signal 10 of the implantable pacing device IPD.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

REFERENCE SIGNS

1 implantable system
2 active housing
3 electrode lead
4 sternum
5, 6 sensing poles
7 shock coil
10 signal
12 shock therapy parameters
14 message
15 remote monitoring system
16 detection unit
18 tachycardia pacing timing unit
20 fault detection device
22 first control unit
24 first stage
26 second stage
28 receiving unit
30 information unit
32 second control unit
34 zone boundary
36 tachycardia detection
38 ventricular tachycardia
40 shock capacitors
42 shock therapy
H heart
ATP anti-tachycardia pacing
ICD implantable cardioverter defibrillator
IPD implantable pacing device
S1-S4 method steps

The invention claimed is:

1. Implantable system for providing anti-tachycardia and/or shock therapy, comprising: an implantable pacing device, in particular an implantable leadless pacemaker, and an implantable cardioverter defibrillator, in particular a non-transvenous implantable cardioverter defibrillator, wherein the implantable pacing device is configured to detect a tachycardia and to provide anti-tachycardia pacing, wherein the implantable pacing device is further configured to signal an unavailability of anti-tachycardia pacing to the implantable cardioverter defibrillator, and wherein the implantable cardioverter defibrillator is configured, in response to the signal of the implantable pacing device, to adjust predetermined shock therapy parameters related to delay of shock therapy.

2. Implantable system of claim 1, wherein the implantable pacing device is configured to stimulate at least one ventricle of a human or animal heart, and wherein the implantable pacing device comprises a configurable tachyarrhythmia detection unit configured to detect a tachycardia and further comprises an anti-tachycardia pacing timing unit configured to deliver an anti-tachycardia pacing sequence in response to tachycardia detection.

3. Implantable system of claim 1, wherein the implantable pacing device comprises a fault detection device configured to detect the unavailability of anti-tachycardia pacing, in particular due to a battery exhaustion and/or fault conditions of the implantable pacing device.

4. Implantable system of claim 1, wherein the implantable pacing device comprises a first control unit configured to block anti-tachycardia pacing delivery after detection of battery exhaustion and/or fault conditions and is configured to signal the unavailability of anti-tachycardia pacing to the implantable cardioverter defibrillator.

5. Implantable system of claim 1, wherein the implantable pacing device is configured to detect a first stage of battery depletion, in which anti-tachycardia pacing is unavailable but anti-bradycardic pacing is available, and wherein the implantable pacing device is configured to detect a second stage of battery depletion, in which both anti-tachycardia pacing and anti-bradycardic pacing are unavailable.

6. Implantable system of claim 1, wherein the implantable pacing device is configured to signal the implantable cardioverter defibrillator by means of intra-body-communication, in particular by means of electrical pulses, communication and/or radio signals.

7. Implantable system of claim 1, wherein the implantable pacing device is configured to signal the unavailability of anti-tachycardia pacing to the implantable cardioverter defibrillator by the implantable pacing device detecting an absence of expected anti-tachycardia pacing, in particular if anti-tachycardia pacing is not provided for a predetermined time period in case of a detected tachycardia.

8. Implantable system of claim 1, wherein the implantable cardioverter defibrillator comprises at least one receiving unit configured to receive information indicating the unavailability of anti-tachycardia pacing and/or anti-bradycardic pacing, from the implantable pacing device.

9. Implantable system of claim 8, wherein the implantable cardioverter defibrillator comprises a second control unit configured to adjust a therapeutic and/or diagnostic behavior of the implantable cardioverter defibrillator upon receiving the information from the implantable pacing device and/or to forward the received information to the remote monitoring system.

10. Implantable system of claim 9, wherein the implantable cardioverter defibrillator is configured to detect the information if one or more expected anti-tachycardia pacing attempts are not sensed by the implantable cardioverter defibrillator.

11. Implantable system of claim 1, wherein the implantable cardioverter defibrillator is configured to shorten or suppress a defibrillation delay when it is detected that anti-tachycardia pacing delivery is unavailable.

12. Implantable system of claim 1, wherein the implantable cardioverter defibrillator is configured to adjust at least one zone boundary for tachycardia detection when it is detected that anti-tachycardia pacing delivery is unavailable.

13. Computer implemented method for providing anti-tachycardia and/or shock therapy, comprising the steps of:

providing an implantable system for providing anti-tachycardia and/or shock therapy, comprising an implantable pacing device, in particular an implantable leadless pacemaker, and an implantable cardioverter defibrillator, in particular a non-transvenous implantable cardioverter defibrillator;

detecting a tachycardia and providing anti-tachycardia pacing, by means of the implantable pacing device;

signaling an unavailability of anti-tachycardia pacing to the implantable cardioverter defibrillator by means of the implantable pacing device; and adjusting predetermined shock therapy parameters related to delay of shock therapy by the implantable cardioverter defibrillator in response to the signal of the implantable pacing device.

14. A non-transitory computer program with program code to perform the method of claim 13 when the computer program is executed on a computer.

15. Computer-readable data carrier containing program code of a non-transitory computer program for performing the method of claim 13 when the computer program is executed on a computer.

* * * * *